United States Patent

Boucher et al.

[11] Patent Number: 5,658,289
[45] Date of Patent: Aug. 19, 1997

[54] LIGAMENT GRAFT PROTECTION APPARATUS AND METHOD

[75] Inventors: James A. Boucher, Clearwater; Brian David Dross, Gulfport; Matthew R. Frushell, Clearwater, all of Fla.

[73] Assignee: Linvatec Corporation, Largo, Fla.

[21] Appl. No.: 552,208

[22] Filed: Nov. 2, 1995

Related U.S. Application Data

[63] Continuation of Ser. No. 126,941, Sep. 24, 1993, abandoned.
[51] Int. Cl.$^6$ .................................................. A61B 17/56
[52] U.S. Cl. ............................. 606/73; 606/104; 606/86
[58] Field of Search ............................ 606/104, 73, 96, 606/99, 86, 79, 72, 65, 53; 623/13

[56] References Cited

U.S. PATENT DOCUMENTS

| | | | |
|---|---|---|---|
| 2,248,054 | 7/1941 | Becker | 606/104 X |
| 4,450,834 | 5/1984 | Fischer . | |
| 4,450,835 | 5/1984 | Asnis et al. . | |
| 4,716,893 | 1/1988 | Fischer et al. . | |
| 4,870,957 | 10/1989 | Goble et al. . | |
| 4,927,421 | 5/1990 | Goble et al. . | |
| 4,927,424 | 5/1990 | McConnell et al. | 606/96 |
| 4,950,270 | 8/1990 | Bowman et al. . | |
| 4,961,421 | 10/1990 | Muller . | |
| 5,049,150 | 9/1991 | Cozad | 606/86 |
| 5,139,500 | 8/1992 | Schwartz | 606/96 |
| 5,152,790 | 10/1992 | Rosenberg et al. | 623/13 |
| 5,211,647 | 5/1993 | Schmieding . | |
| 5,234,434 | 8/1993 | Goble et al. | 606/96 |
| 5,282,802 | 2/1994 | Mahony, III | 606/72 |

FOREIGN PATENT DOCUMENTS

| | | | |
|---|---|---|---|
| 1754088 | 8/1992 | U.S.S.R. | 606/104 |

OTHER PUBLICATIONS

Dawson, Jr. George R., "A Motor Driven Screw Holder and Driver" The Journal of Bone and Joint Surgery, vol. 29, No. 2, Apr. 1947 pp. 527–528.

DePuy Catalogue from 1943. White Type Screw Driver, p. 89.

*Primary Examiner*—Guy V. Tucker
*Attorney, Agent, or Firm*—Gene Warzecha

[57] ABSTRACT

A graft protection device suitable for protecting a bone-tendon-bone graft used during anterior cruciate ligament reconstruction. The graft protection device comprises a distal blocking member, a proximal releasable holding sleeve and an elongated connecting portion connecting the blocking member with the holding sleeve. A radially extending handle is attached to the holding sleeve in order to enable a user to longitudinally and rotationally position the graft protection device along the shaft of an elongated driver when the device is inserted through an opening into a joint. A method of utilizing the graft protection device is also disclosed comprising the steps of guiding a screw/driver/protector assembly along a guide wire into proper position within a bone tunnel, driving the screw into place by turning it and thereby sliding it along the blocking member past a portion of the ligament graft and then locking the guide wire to the driver and removing it along with the driver/protector assembly in a single motion. A lockable, cannulated screw driver is disclosed to facilitate using the graft protection device with the method disclosed herein.

10 Claims, 6 Drawing Sheets

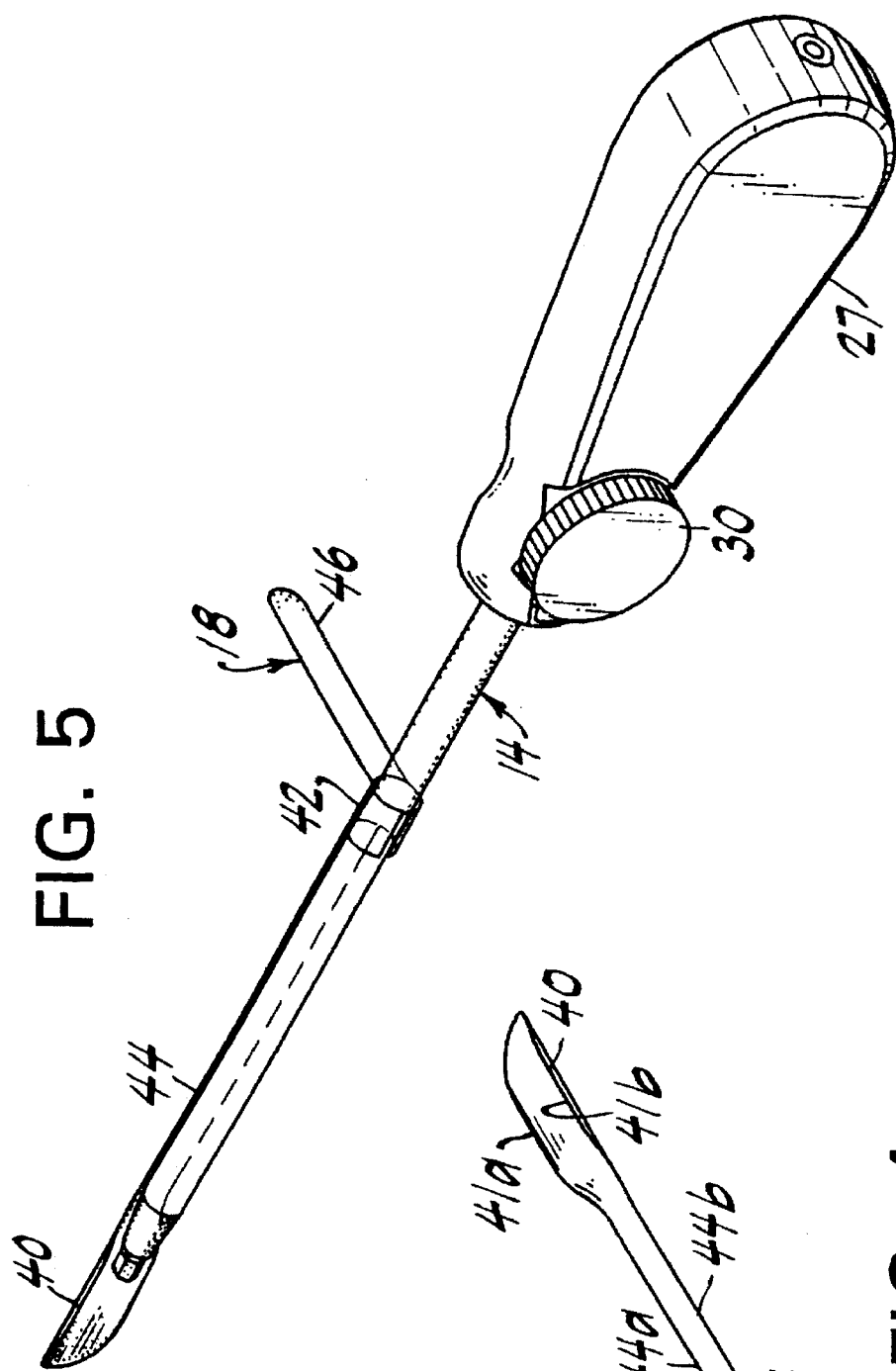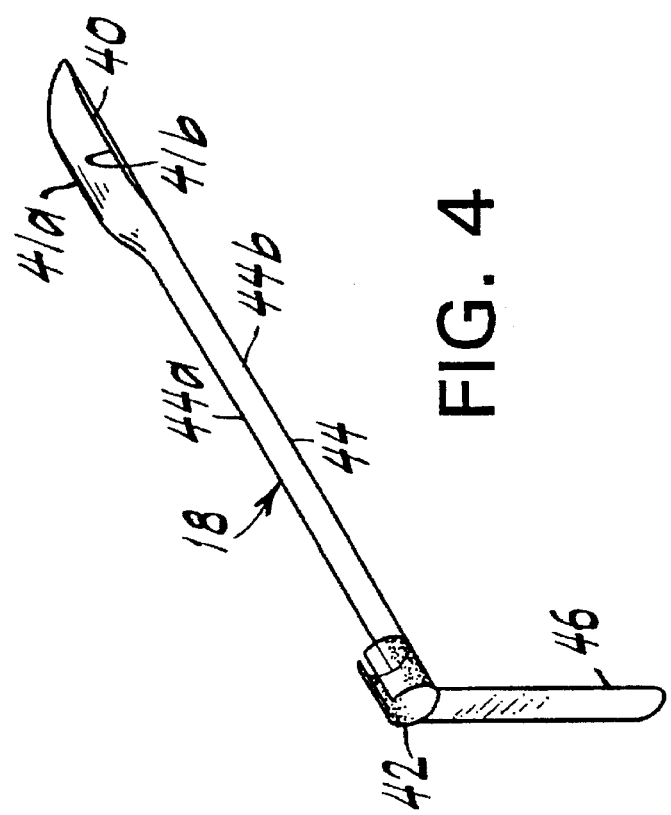

LIGAMENT GRAFT PROTECTION APPARATUS AND METHOD

This is a continuation application of application Ser. No. 08/126,941, filed Sep. 24, 1993, now abandoned.

BACKGROUND OF THE INVENTION

1. Field of the Invention

The invention relates to surgical devices and in particular to instruments used in the arthroscopic repair of ligaments such as anterior cruciate ligaments. More particularly, the invention relates to instruments for securing grafts such as artificial natural or prosthetic ligaments in bone tunnels while protecting the ligament from damaging by the securing device.

2. Description of the Prior Art

As new procedures and instruments continue to be developed for arthroscopically repairing knee ligaments such as anterior cruciate ligaments (ACLs) and posterior cruciate ligaments (PCLs) and as surgeons become familiar with these existing procedures, the need for other new devices becomes apparent.

For example, it is becoming fairly common to repair an ACL with an autograft ligament formed of bone-tendon-bone harvested from the patient's patellar bone, patellar tendon and bone from the tibial tuberosity. Such a graft ligament (which may be an allograft) takes the form of an elongated, natural ligament which has generally rectangularly shaped natural bone blocks at each end. One procedure for accomplishing an arthroscopic ACL repair with such a graft ligament is disclosed in U.S. Pat. Reissue No. 34,293 (Goble et al.), incorporated by reference herein, which describes a surgical method comprising the steps of securing a natural or prosthetic ligament endosteally within a "blind" tunnel segment formed in the femur and an aligned tunnel segment formed in the tibia, both tunnel segments formed through a single incision. In addition to the various ligament fixation devices disclosed in the aforementioned patent, many ACL repair procedures utilize bone-tendon-bone grafts secured by cannulated interference screws guided along elongated guide pins or guide wires into the space between the tunnel wall and the adjacent bone block in order to create an interference fit to retain the bone block within the tunnel. Such a procedure is described in U.S. Pat. No. 4,927,421 (Goble et al.), also incorporated by reference herein.

As surgeons have become adept at performing the aforementioned procedures, a need has become apparent for an improvement by providing a means to protect the graft or artificial ligament as it is being secured within the bone tunnel. Utilizing prior art devices it has been found that the ligament portion of the graft may occasionally be inadvertently cut or nicked by the interference screw threads, thus weakening the attachment of the artificial ligament within the bone. One type of graft protection device has been disclosed in U.S. Pat. No. 5,211,647 (Schmieding) which discloses an elongated, cylindrical cannulated sheath for retaining an interference screw within its distal end. The sheath is formed from plastic and has a portion of its distal tip removed in order to form a cutout through which the threads of the interference screw are exposed in order to enable them to grab the bone as the screw is turned relative to the sheath. The non-cutout portion of the sheath tip lies between the screw and the graft in order to keep the screw from damaging the graft. A screw driver is inserted axially through the sheath and into a drive recess within the interference screw in order to enable the screw to be advanced from the sheath. This device has proven to have too large a diameter for many applications, thereby making it difficult to insert the sheath tip through an opening in the skin and into the joint. This may result in the screw being prematurely pushed out of the sheath by the driver. The small cutout size makes it difficult to reassemble the sheath and screw, especially within the joint. The large size of the device also interferes with the surgeon's visualization of the work site.

Accordingly, it is an object of this invention to produce a graft protection device which overcomes the disadvantages of prior art devices.

It is another object of this invention to produce a graft protection device which provides adequate graft protection while minimizing the size of the device which may lie adjacent an opening in the skin through which the device must extend into a joint.

It is another object of this invention to provide a graft protection device for arthroscopic use with an interference screw wherein the device minimizes the arcuate coverage of the screw while still providing adequate graft protection and adequate retention of the screw on a driving device.

It is also an object of this invention to provide a graft protection device provided with a means by which the interference screw may be retained on the screw driver.

It is also an object of this invention to provide a graft protection device which may be easily moved by a user in order to adjust the longitudinal and rotational position of the device along the shaft of a screw driver.

It is another object of this invention to provide a graft protection device which may perform its intended function while optimizing the surgeon's ability to visualize the work site.

SUMMARY OF THE INVENTION

These and other objects of this invention are achieved by the preferred embodiment disclosed herein which is a graft protection device for protecting an artificial natural or prosthetic ligament graft during the fixation of the ligament graft within a bone tunnel by a bone screw driven between the bone tunnel wall and the graft by an elongated screw driver engaged within a drive recess of the bone screw. The graft protection device comprises an elongated blocking member for contiguously engaging the outer surface of the bone screw, when the bone screw is engaged with the screw driver, while being aligned parallel to and spaced from the axis of the bone screw. The device also comprises a means for releasably holding the elongated blocking member in a predetermined longitudinal and rotational position relative to the screw driver and the screw. An elongated connecting means joins the elongated blocking member with the releasable holding means in order to enable manipulation, from outside the body, of the blocking member adjacent the bone tunnel inside the body.

Another invention disclosed herein is a device which facilitates the use of the graft protector, this device being an elongated, cannulated driver for advancing a cannulated threaded device along a guide wire during a surgical procedure. The cannulated driver comprises a handle having an axially aligned longitudinally extending first throughbore, a hollow elongated shaft secured to the handle and having a second throughbore axially aligned with the first throughbore. The driver also includes a drive tip for receiving the cannulated threaded device, the drive tip being secured to the elongated shaft and having a third throughbore aligned with the second throughbore. The driver is also provided with a locking means for selectively locking the driver against motion relative to a guide wire received within the axially aligned channel formed by first, second or third throughbores. The locking means comprises a user activated control means for being selectively moved by a user between a locked position, in which the guide wire is immovable relative to the driver, and an unlocked position in which the guide wire is movable relative to the driver. An engagement means is connected to the control means for frictionally engaging the guide wire when the control means is in the locked position.

The method of utilizing the graft protection device is also an invention disclosed herein. This preferred method is a method of protecting a ligament graft from a bone screw during fixation of the graft within a bone tunnel by the bone screw being driven by a screw driver into the bone tunnel between the tunnel wall and the graft. The method comprises the steps of providing an elongated graft protector having an elongated blocking member subtending along its length a predetermined arcuate distance, a releasable holding sleeve and an elongated connecting portion joining the blocking member and holding sleeve. The connecting portion subtends an arcuate length less than or equal to that of the blocking member. The method further comprises the steps of releasably securing the graft protector to the screw driver, placing the blocking member of the graft protector into contiguous engagement with the bone screw and rotationally positioning the graft protector adjacent the bone tunnel to place the blocking member between the bone screw and a predetermined portion of the graft.

BRIEF DESCRIPTION OF THE DRAWINGS

FIG. 4 is a perspective view of the graft protection device included with the system shown in FIG. 1.

FIG. 5 is a front perspective view of the screw driver and graft protection device assembled in one orientation.

DESCRIPTION OF THE PREFERRED EMBODIMENT

Figure 1:
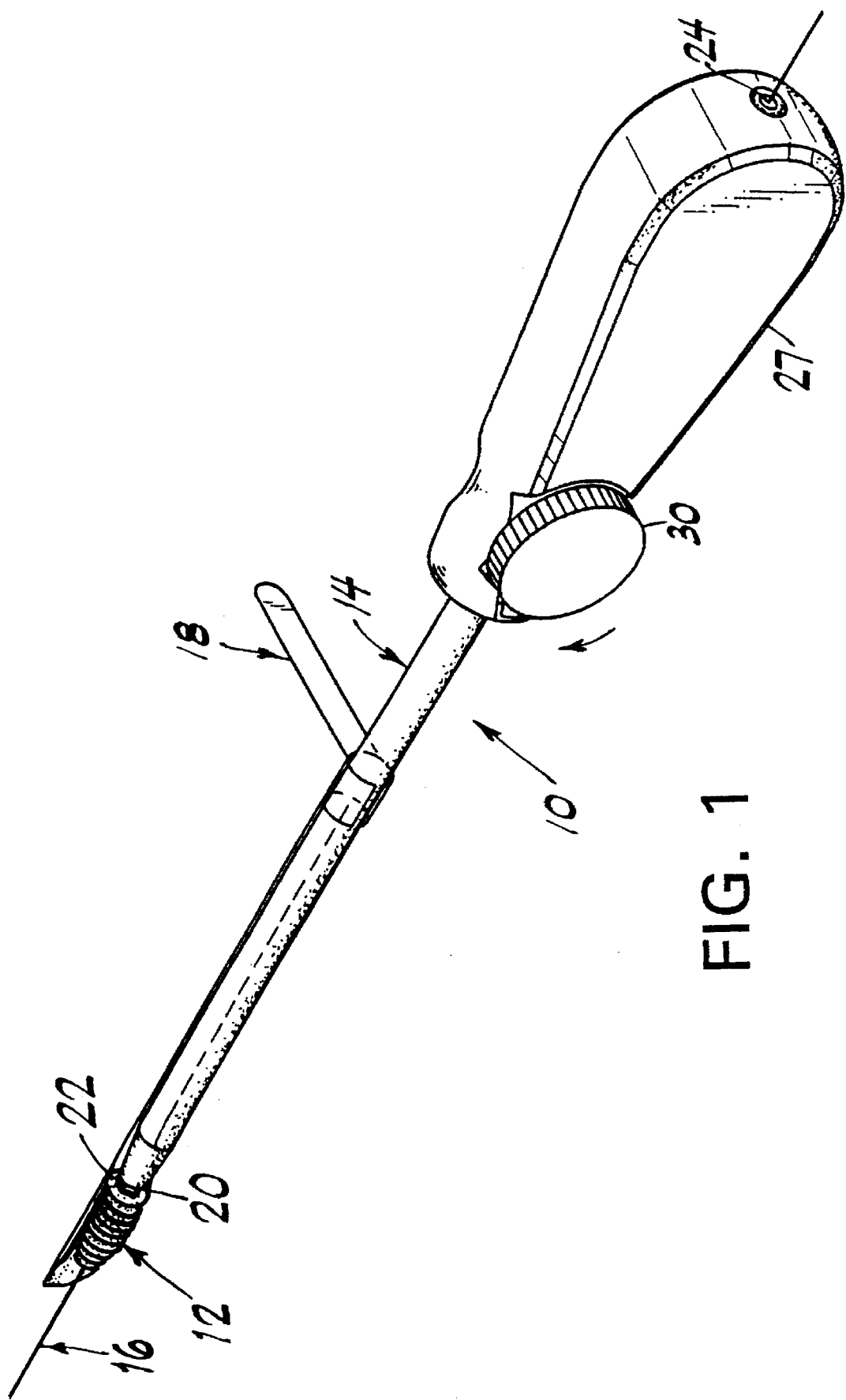
FIG. 1 is a front perspective diagrammatic view of graft protection and fixation system constructed in accordance with the principles of this invention.

Referring now to FIG. 1, there is shown a graft protection and fixation system 10 comprising a cannulated interference bone screw 12, a cannulated screw driver 14, a guide wire 16 and graft protector 18.

Figure 2:
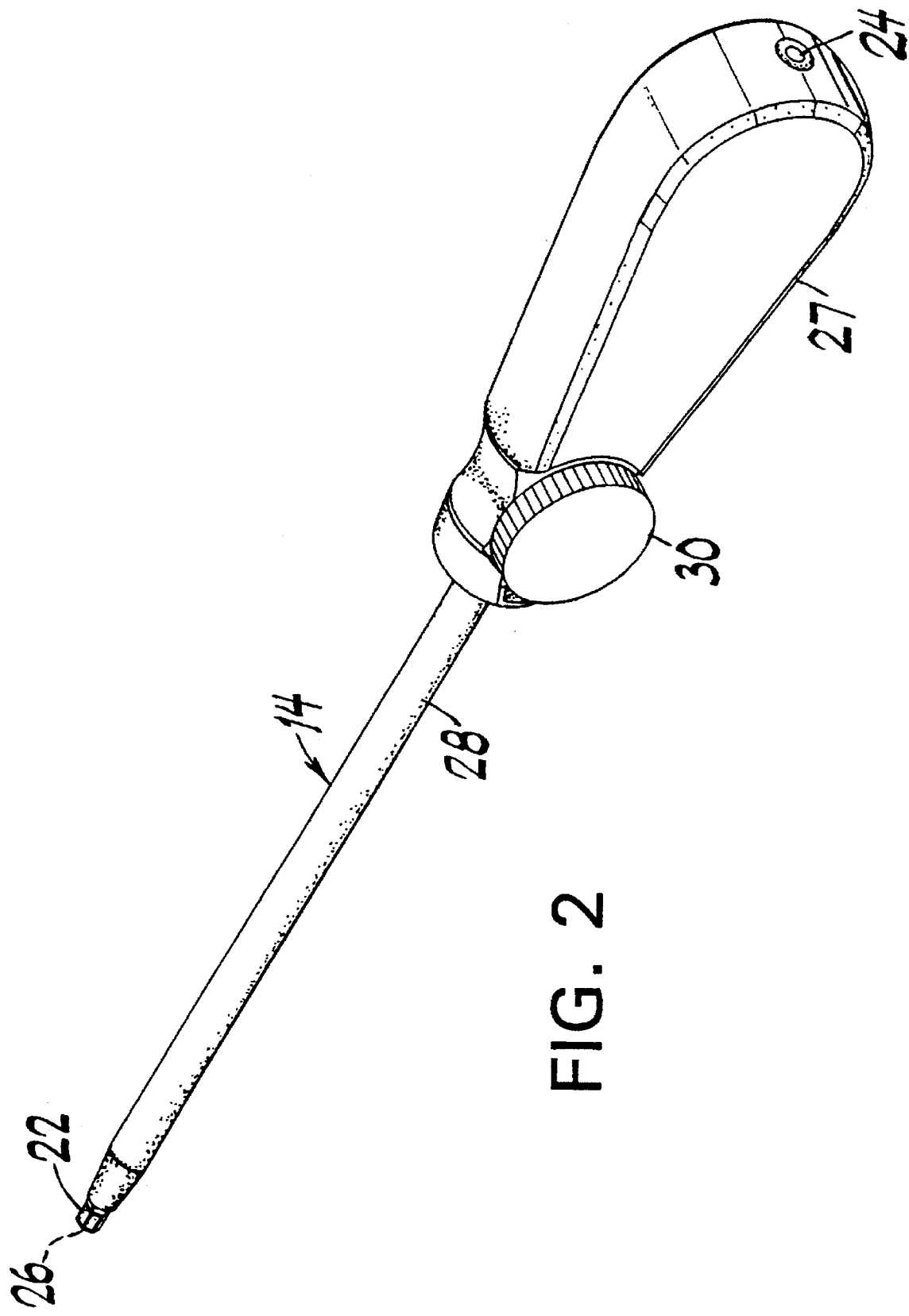
FIG. 2 is a front perspective view of the screw driver portion of the system shown in FIG. 1.

Interference screw 12 is a conventional, cannulated interference screw having an axially aligned, hexagonal drive recess 20 at its proximal end, the drive recess extending into the screw a sufficient distance in order to receive a complementarily shaped drive tip 22 of screw driver 14 (best seen in FIG. 2). Screw 12 has an axial throughbore (not shown) of sufficient diameter to receive a guide wire 16.

Figure 3:
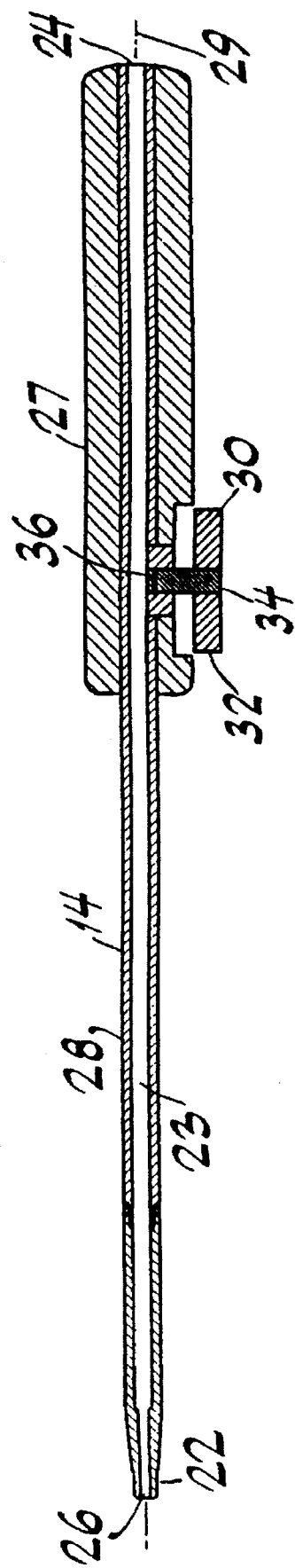
FIG. 3 is a cross-sectional elevation view of the screw driver shown in FIG. 2.

Screw driver 14, more particularly described with reference to FIGS. 2 and 3, has a handle 27, an elongated shaft 28 extending from one end of the handle and a rectilinearly profiled drive tip 26 extending from the end of shaft 28. Screw driver 14 is cannulated along its longitudinal axis 29 to form an axial channel 23 extending from a proximal point 24 through the distal tip 26 in order to receive guide wire 16 therethrough. Locking means 30 is provided on the handle of screw driver 14 at an intermediate point along channel 23 in order to selectively secure guide wire 16 to prevent its longitudinal motion relative to the screw driver. In the preferred embodiment locking means 30 comprises a thumb wheel 32 having an axial threaded shaft 34, the bottom end 36 of which may selectively extend into channel 23 in order to press against and frictionally engage guide wire 16.

FIG. 4 is a perspective view of the graft protection device 18 which comprises a distal blocking member 40, a proximal releasable holding sleeve 42 and an elongated connecting portion 44 securing blocking member 40 to holding sleeve 42. In the preferred embodiment, blocking member 40 is approximately as long as screw 12 and has a thin, arcuate cross-section in order to increase the contact area between the blocking member and the screw and to provide sufficient protection to the ligament portion of the bone-tendon-bone graft by blocking any contact between this portion and the screw. The arcuate cross-section is bounded by parallel edges 41a and 41b which extend along the length of screw 12 a distance long enough to block any contact between the screw and the graft. The arcuate length of blocking member 40 is approximately 180° and the concave surface thereof is smooth in order to enable screw 12 to easily slide along the surface as the screw is turned. To avoid injury to tissue, the distal tip of blocking member 40 is rounded and the proximal ends of edges 41a and 41b gradually blend into the parallel sides of the edges 44a and 44b, respectively, of connecting portion 44. A radially outwardly extending tab 46 serves as a handle to enable a surgeon to manipulate graft protection device 18 in a manner which will be explained below. In the preferred embodiment, graft protection device 18 is integrally formed from a biocompatible material such as stainless steel or any one of a variety of suitable plastic materials. It will be understood that connection portion 44 must be sufficiently long to enable blocking member 40 to be placed adjacent an interference screw at the distal tip of driver 14 while simultaneously enabling handle 46 to be accessible outside the body joint. The connecting portion 44 serves to press blocking member 40 inwardly against screw 12 and also transmits the longitudinal and rotational motion of sleeve 42 to the blocking member. The arcuate length of connecting portion 44 need not be equal to that of blocking member 40 in order to achieve these functions. It is preferable to make the arcuate length of connecting portion 44 less than that of blocking member 40 in order to minimize material usage and resistance to insertion of protector 18 through the chosen skin opening.

Figure 6:
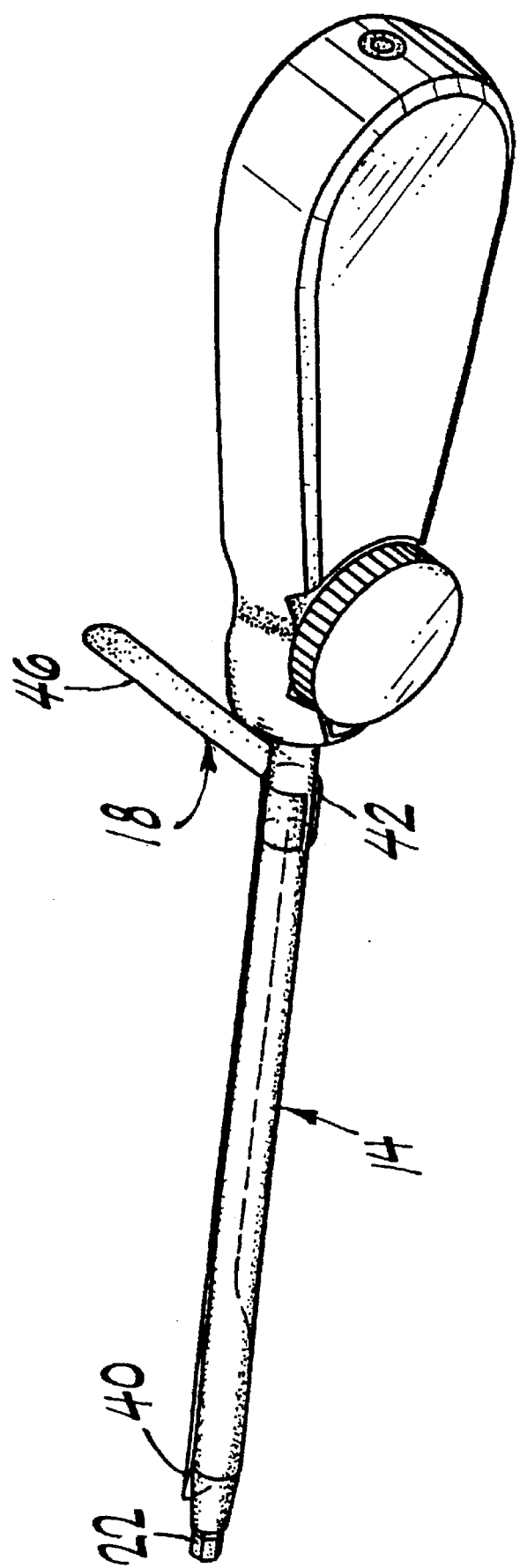
FIG. 6 is a view of the components of FIG. 5 assembled in a different orientation.

FIGS. 5 and 6 show the graft protection device 18 in combination with driver 14 during the initial stages of the novel method of using the invention described herein. As shown in FIG. 5, the proximal end of holding sleeve 42 is placed over the distal tip of the driver shaft and pushed toward the proximal or handle end of the driver to a position as shown in FIG. 6. Holding sleeve 42 has a circular cross-section and is split along a longitudinal line and made normally slightly smaller than the circular cross-section of shaft 28 of the screw driver so that when the two components are mated together graft protection device 18 will be frictionally retained in a given position on the shaft. It will be understood that this friction fit enables graft protection device 18 to be positioned in any longitudinal position along shaft 28 and in any desired rotational position relative to the screw driver 14.

Assembling the various components of this invention is preferably done in a certain order. The graft protection device 18 should first be placed on shaft 28 in order to avoid damaging the threads of screw 12. When graft protection device 18 is slid down along shaft 28 a sufficient distance so that blocking member 40 is behind drive tip 22, the drive recess of interference screw 12 may be placed on tip 22. While holding screw 12 on tip 22, graft protection device 18 is then pushed distally along shaft 28 to a position such as that shown in FIG. 1 where blocking member 40 will be aligned with the axis of the screw and adjacent the lateral side i.e. arcuate outer surface thereof. Graft protection device 18 is constructed of sufficiently rigid material such that connecting portion 44 causes blocking member 40 to press radially inwardly toward the axis of the driver and the screw to thereby apply a friction fit against interference screw 12 to retain it on tip 22. While this frictional engagement exists with any contiguity between the screw and the blocking member, it has been found that providing the blocking member with an arcuate profile facilitates this frictional engagement.

Either before or after assembly of drive tip 22 with interference screw 12, guide wire 16 may be inserted through channel 23 within driver 14 and may be extended beyond the tip of screw 12 a predetermined distance selected by the surgeon. The guide wire may be locked in place by tightening locking means 30.

Figure 7:
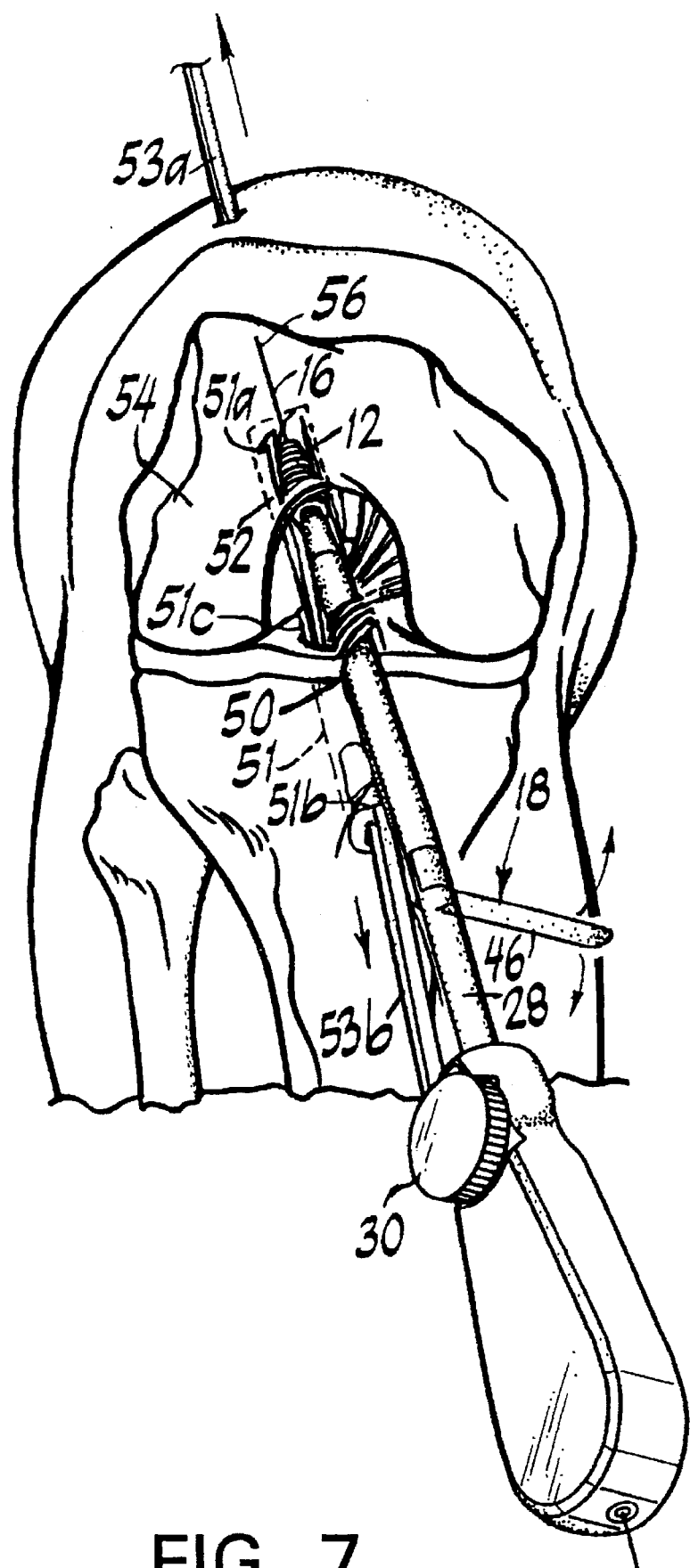
FIG. 7 is a diagrammatic cut-away view of a knee showing a method of using the graft protection and fixation system shown in FIG. 1.

One preferred method for utilizing the graft protection device may be understood by reference to FIG. 7. The use of the graft protection device requires the prior preparation of a bone tunnel and a ligament graft in accordance with conventional procedures outside the scope of this invention. FIG. 7 shows a patient's knee after tibial and femoral bone tunnel segments have been prepared and after a bone-tendon-bone graft 51 has been inserted into the tunnel segments. Graft 51 has a femoral bone block 51a, a tibial bone block 51b and a ligament portion 51c extending between the bone blocks. In some procedures, during fixation tension may be applied to the graft by pulling in the direction of the arrows on sutures or other devices 53a and 53b attached to the bone blocks. The method to be described begins after one bone block end of a ligament graft is placed within a bone tunnel. Once the tunnel is prepared and the graft is in place in tunnel 52 formed in a femur 54, the guide wire 16 is then placed in position so the distal tip 56 of the guide wire is embedded or held against the end of the femoral tunnel while the body of the guide wire extends through either an arthroscopic portal or other opening 50 in the skin so the proximal end of the guide wire is accessible outside the body. For example, guide wire 16 may extend through the incision created in the skin in the process of harvesting the bone-tendon-bone graft. Next, the graft protector 18 is loaded onto the driver shaft 28 and interference screw 12 is placed on drive tip 22. The graft protector 18 is then slid distally along shaft 28 until blocking member 40 lies adjacent screw 12. The driver/screw/protector assembly is then placed onto the proximal end of guide wire 16 and inserted into the joint through the incision or portal 50. (Depending upon the amount of space available or the type of graft being secured, the invention disclosed herein may perform equally well upon insertion through the tibial tunnel segment as well.) If necessary, graft protector 18 is then rotated relative to shaft 28 in order to place blocking member 40 between screw 12 and the ligament graft, adjacent the edge of bone block 51a which is at the entrance to the femoral tunnel. (Note the thickness of the bone block is usually greater than that of the ligament portion, thereby creating an edge where the block meets the ligament.) The driver/screw/protector assembly is then pushed further into the joint in order to engage the screw with the bone block. The graft protector handle 46 should then be held while the screw driver is turned to advance the screw into the femoral tunnel. As the screw is advanced its thread bites into the bone tunnel wall and the bone block while sliding longitudinally relative to blocking member 40 thereby passing past the junction between the bone block and its attached ligament. After the screw is properly placed, drive tip 22 is disengaged from screw 12, the locking mechanism 30 is locked onto guide wire 16 and the driver, protector and guide wire may be removed from the joint in one motion.

An alternate method of using the invention also comprises the steps of assembling the driver, screw and graft protector prior to loading the guide wire into the axial channel of the driver. In this method, the guide wire is extended beyond the distal tip of screw 12 to a predetermined length and then locked into place prior to insertion into the joint. The entire assembly with the extending guide wire is inserted into the joint through the desired opening and the graft protector is oriented between the graft and the screw as in the previous method. The entire assembly is then advanced toward the femoral tunnel and the extended portion of the guide wire is inserted into the tunnel parallel to the bone block between the bone block and the wall of the tunnel. The guide wire locking mechanism may then be loosened if it is desired to have the guide contact the end of the tunnel and the screw driver turned to advance the screw into proper position. The drive tip is disengaged from the screw, the driver is locked onto the guide wire and the entire assembly is removed with the guide wire, leaving the screw in place. This method also enables this invention to be used in a manner similar to a known non-cannulated interference screw which is provided with a drive recess at its proximal end and a short, blunt nose at its distal tip. Leaving guide wire 16 extending only a short distance beyond the distal tip of screw 12 produces a similar device.

While the invention is described herein with respect to an interference type bone screw, it is equally applicable to other graft fixation devices which may make it necessary or desirable to block or protect the graft from the fixation device. The invention would also be useable without cannulated fixation devices or drivers.

It will be understood by those skilled in the art that numerous improvements and modifications may be made to the preferred embodiment of the invention disclosed herein without departing from the spirit and scope thereof.

What is claimed is:

1. In combination, a graft protection device and an elongated screw driver, said graft protection device for protecting an artificial natural or prosthetic ligament graft during the fixation of the ligament graft within a bone tunnel by a bone screw driven between the bone tunnel wall and the graft by said elongated screw driver, said screw driver having a proximal end and a distal end, a handle at said proximal end, a drive tip at said distal end, and a cylindrical shaft interposed between said proximal end and said distal end, said drive engagable within a drive recess of the bone screw, said bone screw having an axis and an arcuate outer surface, said graft protection device comprising:

an elongated blocking member for touching approximately 180° of the arcuate outer surface of the bone screw, when the bone screw is engaged with the screw driver, while being aligned parallel to and spaced from the axis of the bone screw;

holding means for slidably frictionally engaging said cylindrical shaft of said screw driver, said holding means comprising an inner cylindrical surface adapted to substantially surround said cylindrical shaft and slide therealong, said holding means for releasably holding said elongated blocking member in a first predetermined longitudinal and rotational position relative to the screw driver, said frictional engagement of said holding means and said cylindrical shaft being adapted to be selectively overcome by sliding said holding means relative to said shaft to move said elongated blocking member to a second predetermined longitudinal and rotational position relative to said screw driver; and elongated connecting means having an axis and extending longitudinally along said axis, said elongated connecting means joining said elongated blocking member with said releasable holding means.

2. A graft protection device according to claim 1 wherein said elongated blocking member has an arcuate cross-section within a plane perpendicular to the axis of said elongated connecting means.

3. A graft protection device according to claim 2 wherein said elongated blocking member extends a predetermined longitudinal distance parallel to the axis of said elongated connecting means.

4. A graft protection device according to claim 1 wherein said means for releasably holding said elongated blocking member comprises a tubular sleeve provided with a longitudinally extending gap, the inside dimensions of said tubular sleeve normally being slightly less than the outside dimensions of the portion of said driver onto which said sleeve is received.

5. A graft protection device according to claim 1 further comprising:

radially outwardly extending handle means secured to said releasable holding means for enabling a user to grasp same and thereby move said device longitudinally or arcuately relative to the screw driver and the screw in order to position said elongated blocking member in a predetermined orientation relative to the graft.

6. In combination, a graft protection device and an elongated screw driver, said graft protection device for protecting an artificial natural or prosthetic ligament graft during the fixation of the ligament graft within a bone tunnel by a bone screw driven between the bone tunnel wall and the graft by said elongated screw driver, said screw-driver having a proximal end and a distal end, a handle at said proximal end, a drive tip at said distal end, and a shaft interposed between said proximal end and said distal end, said drive tip engagable within a drive recess of the bone screw, said bone screw having an axis and an arcuate outer surface, said graft protection device comprising:

an elongated blocking member for contiguously engaging a predetermined portion of the arcuate outer surface of the bone screw, when the bone screw is engaged with the screw driver, while being aligned parallel to and spaced from the axis of the bone screw, said elongated blocking member having a first predetermined arcuate cross-section;

holding means for slidably frictionally engaging said shaft of said screw driver and for releasably holding said elongated blocking member in a first predetermined longitudinal and rotational position relative to the screw driver, said frictional engagement of said holding means being adapted to be selectively overcome by sliding said holding means relative to said shaft to move said elongated blocking member to a second predetermined longitudinal and rotational position relative to the screw driver; and elongated connecting means extending longitudinally along an axis and joining said elongated blocking member with said releasable holding means, said elongated connecting means having a second predetermined, arcuate cross-section which is smaller than said first predetermined arcuate cross-section.

7. A graft protection device according to claim 6 wherein said elongated blocking member has an arcuate cross-section less than or equal to 180°.

8. A graft protection device according to claim 7 wherein the thickness of at least a portion of said elongated connecting means has an arcuate cross-section within a plane perpendicular to the axis of said elongated connecting means less than or equal to that of said blocking member.

9. In combination, a system for driving a ligament fixation device into a bone tunnel adjacent an artificial natural or prosthetic ligament graft and protecting the graft from the fixation device comprising:

a cannulated driver comprising:
an elongated hollow shaft having a distal tip adapted to engage a bone screw;

a cannulated bone screw having an axis, a distal tip and a proximal end comprising:
a generally cylindrical body extending between said distal tip and proximal end, said body provided with at least one thread on its outer surface;
a drive recess within said proximal end for receiving the distal tip of said driver;

a guide wire for being received within said driver and said bone screw;

a graft protection device comprising:
an elongated blocking member for contiguously engaging approximately 180° of the arcuate outer surface of the bone screw while being aligned parallel to and spaced from the axis of the bone screw;
means for releasably holding said blocking member in a predetermined longitudinal and rotational position relative to the screw driver;
elongated connecting means joining said blocking member with said releasable holding means.

10. The combination of claim 9 further comprising means for locking the guide wire to prevent its movement relative to the driver.

* * * * *